United States Patent [19]
Silverstrini

[11] Patent Number: 5,888,243
[45] Date of Patent: Mar. 30, 1999

[54] HYBRID INTRASTROMAL CORNEAL RING

[75] Inventor: Thomas A. Silverstrini, Alamo, Calif.

[73] Assignee: KeraVision, Inc., Santa Clara, Calif.

[21] Appl. No.: 469,845

[22] Filed: Jun. 6, 1995

Related U.S. Application Data

[62] Division of Ser. No. 927,165, Aug. 7, 1992, abandoned.

[51] Int. Cl.⁶ .................................................. A61F 2/14
[52] U.S. Cl. ............................................................. 623/5
[58] Field of Search ........................................ 623/4, 5, 6

[56] References Cited

U.S. PATENT DOCUMENTS

| | | | |
|---|---|---|---|
| 4,316,292 | 2/1982 | Alexeev . | |
| 4,439,196 | 3/1984 | Higuchi | 604/890 |
| 4,452,235 | 6/1984 | Reynolds | 623/5 |
| 4,455,143 | 6/1984 | Theeuwes et al. | 604/890 |
| 4,624,669 | 11/1986 | Grendhal | 623/5 |
| 4,647,282 | 3/1987 | Federov et al. | 623/4 |
| 4,671,276 | 6/1987 | Reynolds . | |
| 4,688,570 | 8/1987 | Kramer et al. . | |
| 4,693,939 | 9/1987 | Ofstead | 623/5 |
| 4,709,996 | 12/1987 | Michelson | 623/16 |
| 4,731,080 | 3/1988 | Galin | 623/6 |
| 4,766,895 | 8/1988 | Reynolds . | |
| 4,799,931 | 1/1989 | Lindstrom | 623/5 |
| 4,815,463 | 3/1989 | Hanna . | |
| 4,819,617 | 4/1989 | Goldberg et al. | 623/6 |
| 4,851,003 | 7/1989 | Lindstrom | 623/5 |
| 4,941,093 | 7/1990 | Marshall et al. | 606/5 |
| 4,961,744 | 10/1990 | Kilmer et al. | 606/166 |
| 4,976,719 | 12/1990 | Siepser | 606/151 |
| 4,983,181 | 1/1991 | Civerchia | 623/5 |
| 5,067,961 | 11/1991 | Kelman et al. | 623/15 |
| 5,090,955 | 2/1992 | Simon | 606/107 |
| 5,098,443 | 3/1992 | Parel et al. | 623/4 |
| 5,300,114 | 4/1994 | Gwon et al. | 623/5 |
| 5,372,580 | 12/1994 | Simon et al. | 606/107 |
| 5,391,201 | 2/1995 | Barrett et al. | 623/5 |
| 5,405,384 | 4/1995 | Silvestrini | 623/5 |

FOREIGN PATENT DOCUMENTS

| | | |
|---|---|---|
| 0420549 | 4/1991 | European Pat. Off. . |
| 2608041 | 6/1988 | France . |
| 2095119 | 12/1981 | United Kingdom . |
| WO 92/00112 | 1/1992 | WIPO . |

OTHER PUBLICATIONS

Temirov et al., "Refractive circular tunnel keroplasty in the correction of high myopia" *Vestnki Oftalmologii* (1991) 3:23–31.

Simón et al., "Refractive remodelling of the cornea by intrastromal rings" *Abstracts: Eighth International Congress of Eye Research*, Proceedings of the International Society for Eye Research, San Francisco, California, USA, Sep. 4–8, 1988, vol. V, (abstract No. 47).

Simón et al., "Refractive remodelling of the cornea by intrastromal rings" *The Association for Research in Vision and Ophthalmology*, Annual Spring Meeting, Sarasota, Florida, USA, Apr. 30–May 5, 1989, p. 187, (abstract 43).

Blavatskaia, "The use of intralamellar homoplasty in order to reduce refraction of the eye" *Überstzt. Aus. Oftalmol. Zh.* (1966) 7:530–537 which was apparently translated to *Arch. Soc. Ophthalmol.* (1988) 6:311–325. A complete English translation was previously enclosed.

English translation of Brazilian Patent No. BR 8705060 (Mar. 21, 1989).

Hartmann et al., "Intrastromal implantation of an adjustable plastic ring to alter the corneal refraction" delivered by H. Freyler et al., Congress for German Society for Intraocular Lens Implantation, Mar. 1989, pp. 465–475 (English translation enclosed).

*Primary Examiner*—Randy C. Shay
*Attorney, Agent, or Firm*—Morrison & Foerster LLP

[57] ABSTRACT

This invention is an intrastromal corneal ring housing comprising at least one outer layer of a physiologically compatible polymer having a low modulus of elasticity, which polymer may be hydratable and may be hydrophilic. The inner portion of the hybird intrastromal corneal ring may be hollow or may contain one or more physiologically compatible polymers.

45 Claims, 4 Drawing Sheets

HYBRID INTRASTROMAL CORNEAL RING

This application is a division of application Ser. No. 07/927,165 filed Aug. 7, 1992, now abandoned.

FIELD OF THE INVENTION

This invention is a hybrid intrastromal corneal ring ("ICR") comprising at least one outer layer of a physiologically compatible polymer having a low modulus of elasticity, which polymer may be hydratable and may be hydrophilic. The inner portion of the ICR may be hollow or may contain one or more physiologically compatible polymers.

BACKGROUND OF THE INVENTION

Anomalies in the overall shape of the eye can cause visual disorders. Hyperopia ("farsightedness") occurs when the front-to-back distance in the eyeball is too short. In such a case, parallel rays originating greater than 20 feet from the eye focus behind the retina. In contrast, when the front-to-back distance of eyeball is too long, myopia ("nearsightedness") occurs and the focus of parallel rays entering the eye occurs in front of the retina. Astigmatism is a condition which occurs when the parallel rays of light do not focus to a single point within the eye, but rather have a variable focus due to the fact that the cornea is aspherical and refracts light in a different meridian at different distances. Some degree of astigmatism is normal, but where it is pronounced, the astigmatism must be corrected.

Hyperopia, myopia, and astigmatism are usually corrected by glasses or contact lenses. Surgical methods for the correction of such disorders are known. Such methods include radial keratotomy (see, e.g., U.S. Pat. Nos. 4,815,463 and 4,688,570) and laser corneal ablation (see, e.g., U.S. Pat. No. 4,941,093).

Another method for correcting those disorders is through the implantation of polymeric rings in the eye's corneal stroma to change the curvature of the cornea. Previous work involving the implantation of polymethylmethacrylate (PMMA) rings, allograft corneal tissue, and hydrogels is well documented. One of the ring devices involves a split ring design which is inserted into a channel previously dissected in the stromal layer of the cornea. A minimally invasive incision is used both for producing the channel and for implanting the implant.

The use of ICRs made completely of certain hard, hydrophobic polymers is known. For instance, in the article "Intrastromal Implantation Eines Justierbaren Kunststofforings Zur Hornhautrefraktionsanderung", Hartmann et al., Kongress der Deutschen Gesellschaft fur Intraokularingen Implantation, delivered by H. Fryler et al., Springer-Verlag, Wien, pages 465–475, the use of intrastromal ring implants of rings of silicone, polymethylmethacrylate ("PMMA"), and fluorocarbons (TEFLON, PTFE, available from DuPont). Other disclosures of the use of PMMA in such intrastromal rings is found in U.S. Pat. No. 4,452,235 to Reynolds; U.S. Pat. No. 4,671,276 to Reynolds; U.S. Pat. No. 4,766,895 to Reynolds; and U.S. Pat. No. 4,961,744 to Kilmer et al. These documents do not suggest the use of multiple-layers of differing materials in the ICRS.

The use of soft polymers as intrastromal inserts is not widely known. For instance, U.S. Pat. No. 5,090,955 to Simon, suggests an ICR which is made by introducing a settable polymer into an intrastromal channel which has been previously made and allowing the polymer to set. This procedure does not allow the surgeon to specify the size of the resulting ring nor is it a process which allows control of the flowing polymer within the eye.

Temirov et al, "Refractive circular tunnel keroplasty in the correction of high myopia", Vestnik Oftalmologii 1991: 3-21-31, suggests the use of collagen thread as ICR material.

They specifically do not suggest the use of soft or hydrophilic polymers insertable into the cornea as ICRs.

SUMMARY OF THE INVENTION

This invention is a hybrid intrastromal corneal ring comprising at least one outer layer of a soft, low modulus, often hydrophilic, physiologically compatible polymer.

The portion of the ICR inside that outer layer may be hollow and adapted to be fillable with a biologic agent, drug or other liquid, emulsified, or time-release eye treatment material. The inner portion may comprise variously a core of a high modulus, physiologically compatible polymer or a further composite of a low modulus polymer or a high modulus polymer core or a high modulus polymer or a low modulus polymer core. The inner portion may comprise a polymeric material which is polymerized in situ after introduction into a hollow center layer.

The term "high modulus polymer" is mean to include physiologically compatible polymers such as PMMA; TEFLON; certain longer chain silicones; polycarbonate; and polyolefins such as polyethylene, polypropylene, polybutylene, their mixtures or other polyolefin interpolymers. The term "low modulus polymer" is meant to include physiologically compatible polymers and hydrogels, such as polyhydroxyethyl methacrylate ("poly-HEMA") or polyvinylpyrrolidone ("PVP") or elastomeric materials and biologic polymers such as crosslinked dextran, hyaluronic acid, and heparin or the like. The low modulus hydratable polymers, in any case, may be of the type which is sufficiently cross-linked such that they do not swell upon contact with water (and subsequent hydration) or of the type which swells when hydrated. Additionally, the class of low modulus polymers is meant to include elastomeric polymers, e.g., latex rubber, colloids of polyester and polyether, polyurethanes, lower molecular weight silicones, isoprene, and the like, which are stable and physiologically compatible. Finally, the low modulus polymer may be a reinforced hydrogel such as an interpenetrating network of polymerized vinyl pyrrolidone and methyl methacrylate.

Our ICRs may be implanted into the stroma using a number of known techniques. If hydratable polymers are used, they may be hydrated before or after introduction into the intrastromal passageway created by the surgical device used to introduce these devices into the eye. If the outer layer is hydrated before insertion into the eye, the final size of the ring is set before that insertion. If the hydratable polymers are allowed to hydrate within the corneal space, the device (if appropriate polymers are chosen) will swell within the eye to its final size. If prehydrated, the outer layer often provides a measure of lubricity to the ICR, allowing it to be inserted with greater ease. Other of the noted low modulus polymers may also provide such lubricity.

This invention allows for adjustment of ICR thickness and diameter and provides a softer interface between a harder polymer core and corneal tissue.

DESCRIPTION OF THE INVENTION

Prior to explaining the details of the inventive devices, a short explanation of the physiology of the eye is needed to appreciate the functional relationship of the ICR to the eye.

Figure 1:
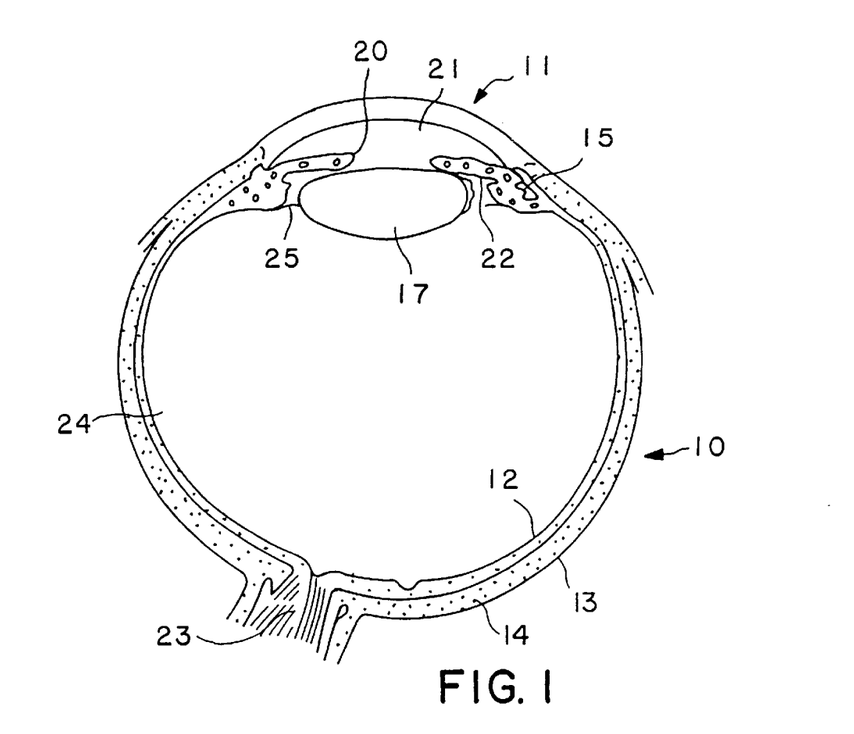
FIG. 1 is a schematic illustration of a horizontal section of the eye.

FIG. 1 shows a horizontal cross-section of the eye with the globe (10) of the eye resembling a sphere with an anterior bulged spherical portion representing the cornea (11).

The globe (10) of the eye consists of three concentric coverings enclosing the various transparent media through which the light must pass before reaching the light-sensitive retina (12). The outermost covering is a fibrous protective portion the posterior five-sixths of which is white and opaque and called the sclera (13), and sometimes referred to as the white of the eye where visible to the front. The anterior one-sixth of this outer layer is the transparent cornea (11).

A middle covering is mainly vascular and nutritive in function and is made up of the choroid (14), ciliary body (15), and iris (16). The choroid generally functions to maintain the retina (12). The ciliary body (15) is involved in suspending the lens (17) and accommodation of the lens. The iris (16) is the most anterior portion of the middle covering of the eye and is arranged in a frontal plane. It is a thin circular disc similar in function to the diaphragm of a camera, and is perforate near its center by a circular aperture called the pupil (20). The size of the pupil varies to regulate the amount of light which reaches the retina (12). It contracts also to accommodation, which serves to sharpen the focus by diminishing spherical aberration. The iris divides the space between the cornea (11) and the lens (17) into an anterior chamber (21) and posterior chamber (22). The innermost portion of covering is the retina (12), consisting of nerve elements which form the true receptive portion for visual impressions.

The retina (12) is a part of the brain arising as an outgrowth from the fore-brain, with the optic nerve (23) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (24) is a transparent gelatinous mass which fills the posterior four-fifths of the globe (10). At its sides it supports the ciliary body (15) and the retina (12). A frontal saucer-shaped depression houses the lens.

The lens (17) of the eye is a transparent bi-convex body of crystalline appearance placed between the iris (16) and vitreous body (24). Its axial diameter varies markedly with accommodation. A ciliary zonule (25), consisting of transparent fibers passing between the ciliary body (15) and lens (17) serves to hold the lens (17) in position and enables the ciliary muscle to act on it.

Referring again to the cornea (11), this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
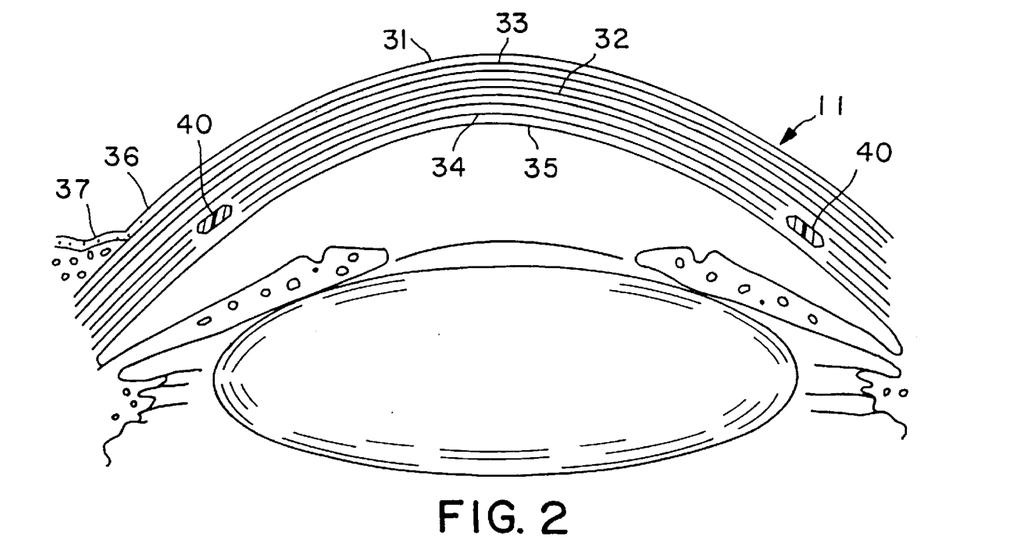
FIG. 2 is a schematic illustration of the anterior portion of the eye showing the various layers of the cornea.

FIG. 2 is a more detailed drawing of the anterior portion of the globe showing the various layers of the cornea (11) making up the epithelium (31) and the general placement of the ICR (40). Epithelial cells on the surface thereof function to maintain transparency of the cornea (11). The e epithelial cells are rich in glycogen, enzyme and acetylcholine and their activity regulates t corneal corpuscles and controls the transport of water and electrolytes through the lamellae of the stroma (32) of the cornea (11).

An anterior limiting lamellae (33), referred to as Bowman's membrane or layer, is positioned between the epithelium (31) and the stroma (32) of the cornea. The stroma (32) is made up of lamellae having bands of fibrils parallel to each other and crossing the whole of the cornea. While most of the fibrous bands are parallel to the surface, some are oblique, especially anteriorly. A posterior limiting lamina (34) is referred to as Descemet's membrane. It is a strong membrane sharply defined from the stroma (32) and resistant to pathological processes of the cornea.

The endothelium (35) is the most posterior layer of the cornea and consists of a single layer of cells. The limbus (37) is the transition zone between the conjunctiva and sclera on the one hand and the cornea (11) on the other.

Figure 3:
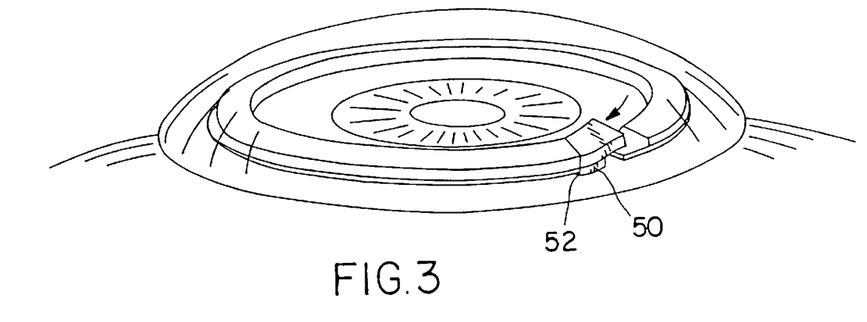
FIG. 3 shows the step of inserting the inventive ICR through an incision in the cornea.

FIG. 3 shows the completion of the step of inserting the hybrid ICR into the corneal stroma. Techniques such as that shown in our copending application Ser. No. 07/867,745, entitled CORNEAL VACUUM CENTERING GUILD AND DISSECTOR, filed Apr. 10, 1992, (attorney docket no. 25169-20006.00), are suitable for preparing the eye and inserting the ICR into the appropriately prepared interlamellar stromal channel. Generally the ICR (50) is installed in the following manner: A small radial incision (52) is made at the corneal radius in which the ICR is ultimately to be installed about the cornea. A dissector in the form of a split ring having a point suitable for producing the interlamellar channel in the corneal stroma is introduced into the stromal space through the small incision. It is then rotated in such a fashion that a generally circular channel is formed completely encircling the cornea. The dissector is then rotated in the opposite direction to withdraw it from the tunnel or channel thus formed. An ICR is then introduced into the circular channel and joined. at its ends. Hybrid ICRs having partially hydrated polymers on their outer periphery are typically slippery and consequently may be introduced into the interlamellar tunnel with great ease. It is usually desirable to (at least partially) hydrate the hybrid ICR in that, otherwise, the ICR during its traverse through the tunnel may desiccate the path and begin to stick to the interior wall of the tunnel. The ICR may be lubricated with suitable ocular lubricants such as hyaluronic acid, methylethyl cellulose, dextran solutions, glycerine solutions, polysaccharides, or oligosaccharides upon its introduction to help with the insertion particularly if one wishes to insert the hybrid ICR without any hydration.

Figure 4:
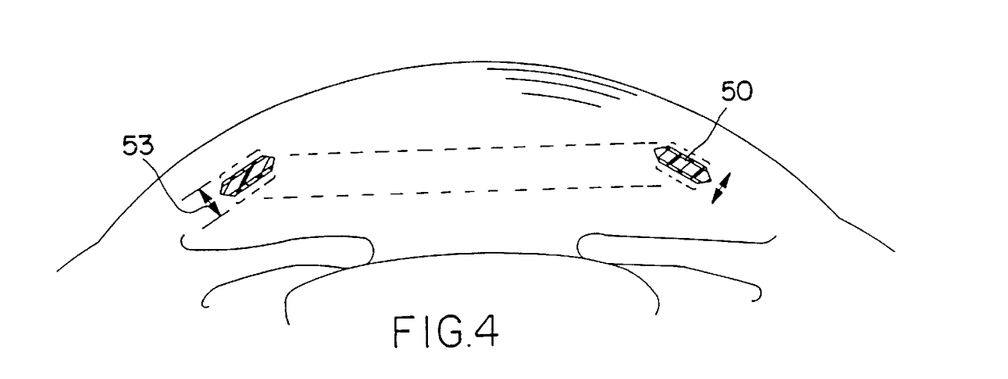
FIG. 4 shows, in partial cross-section, the anterior portion of an eye with the hybrid ICR installed.

FIG. 4 shows, in cross-section, the anterior portion of the eye with the hybrid ICR (50) inserted. Subsequent to the insertion, the ICR (50) will swell to its final size or thickness (53) within the eye. This swelling permits the inclusion of larger ICRs than would normally be accommodated within normal sized intrastromal channels.

Figure 5A:
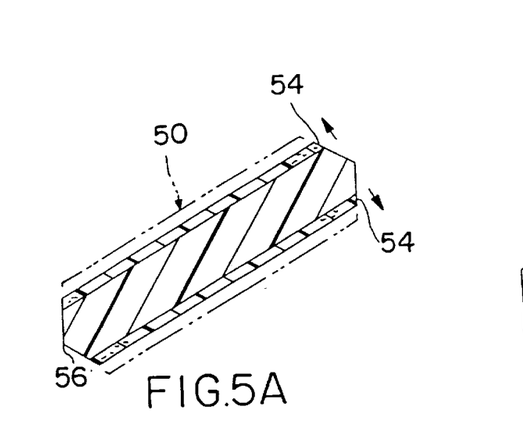
FIGS. 5A and 5B show, in cross-section, respectively, an unhydrated and a hydrated ring in which the hydratable, low modulus polymer is placed on only two surfaces.

FIG. 5A shows in cross-section the hybrid ICR having inner and outer faces (54) comprising polymers having low moduli of elasticity. Low modulus polymers are those having a modulus of elasticity below about 3.5 kpsi, more preferably between 1 psi and 1 kpsi, and most preferably between 1 psi and 500 psi. They must be physiologically compatible with the eye. Most polymeric materials used in soft contact lenses are suitable for the outer layer contemplated in this invention. In addition, the class includes physiologically compatible elastomers such a polyacrylates, silicones, isoprene, and the like. Additionally, low modulus polymers include biologic polymers such as crosslinked dextran, crosslinked heparin or hyaluronic acid.

The inner portion or core (56) as shown in FIG. 5A is a physiologically compatible polymer having a high modulus of elasticity. A high modulus of elasticity is considered to be greater in value than about 3.5 kpsi, preferably 5–12 kpsi, and most preferably 8–10 kpsi. These polymers are typically stiffer and may be materials such as polymethyl methacrylate (PMMA), TEFLON (PTFE), longer chain silicone polymers such as are used in hard contact lenses. Additionally, suitable polymers include polycarbonates; polyolefins such as polyethylene, polypropylene, and polybutylene, their mixtures and polyolefin interpolymers, block copolymers and the like.

The extent to which the outer layers swell upon hydration is dependent upon the type of polymer chosen and, when the polymer is hydratable, upon the amount of cross-linking found in the outer layers (54), and on the thickness of the layer. Generally speaking, the more highly linked the hydratable polymer, the smaller the amount of volume change upon hydration. Conversely, a polymer having only sufficient cross-linking for strength in the service in which this device is placed, will have a somewhat lower level of cross-linking. Alternatively, a substantially nonswellable polymer system may be formed of a hydrogel physically interpenetrated by another polymer which does not hydrate, e.g., polyHEMA, with polyacylnitrite.

The thickness of the outer layer depends in large function upon the intended use of the ICR. For instance if the outer layer is to be used as a container for an inner volume of a settable polymer or drug, the outer layer may be relatively thicker. If the outer layer is used to provide a swellable outer layer which does not add significantly to the size of the ICR or is used functionally as a lubricant layer, the outer layer may be quite thin even to the point of a layer of minimum coverage, perhaps as thin as a molecule thick.

Figure 5B:
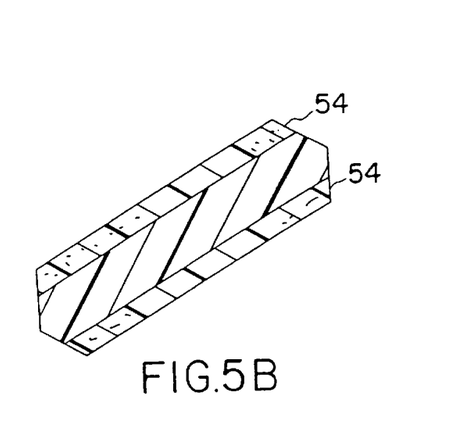

FIG. 5B shows the hybrid ICR of FIG. 5A after it has been completely hydrated and the polymer faces (54) have swollen to their largest extent.

The inventive device shown in FIGS. 5A and 5B may also be used in the instance where a low modulus covering is not placed over the entire outside surface of the ICR. For instance, to alleviate astigmatism, an ICR having a thick portion and a thin portion may be desired. An ICR having an inner core of a high modulus polymer and an outer covering of a swellable polymer might be chosen. The surgeon would remove a portion of the ICR's exterior coating or face prior to introducing the ICR into the eye. Such an ICR and its use are described more fully in co-pending Ser. No. 07/939,492, entitled ASTIGMATIC CORRECTING INTRASTROMAL CORNEAL RING, filed Sep. 3, 1992, (attorney docket number 25169-20008.00).

Figure 6:
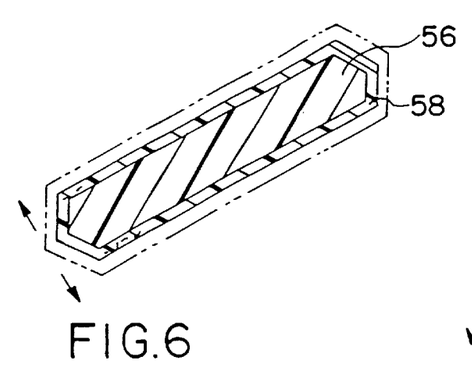
FIG. 6 shows in cross-section an unhydrated hybrid ICR in which the hydratable, low modulus polymer completely coats the ring.

FIG. 6 shows a hybrid ICR in which the core (56) is of high modulus polymeric material such as mentioned above. In this variation the outer surface is completely coated with a swellable polymer or polymeric gel such as those discussed above. Again, the composition of outer covering (58) may be of a hydratable polymer system which is sufficiently cross-linked that the polymer does not swell appreciably upon hydration. Alternatively, the covering (58) may be cross-linked only so much as to allow substantial swelling of the outer covering either before or after insertion into the eye.

Figure 7:
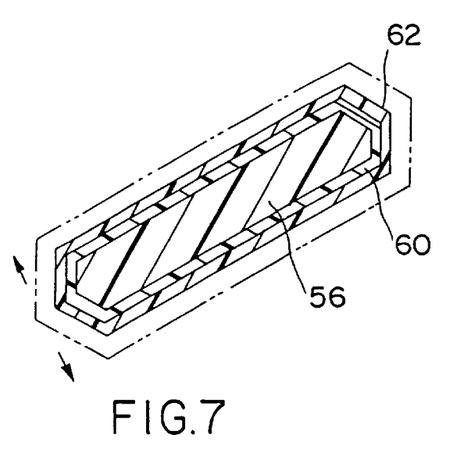
FIG. 7 shows a multiply-coated ICR.

FIG. 7 shows another variation of the inventive hybrid ICR. In this variant of the inventive hybrid ICR, the inner high modulus core (56) is surrounded by more than one layer, specifically, an intermediate layer (60) and an outer layer (62). This hybrid ICR may be appropriate when the outer layer (62) is difficult to bond to the core (56). An intermediate layer (60) which bonds both to the core (56) and to the outer layer (62) may be used. Intermediate layer (60) typically would not be a polymer which swells appreciably upon hydration lest it split outer layer (62). Outer layer (62) may either swell upon hydration, as is shown in FIG. 7, or may remain at approximately the same size upon hydration if a suitably low modulus polymer system is chosen.

Figure 8:
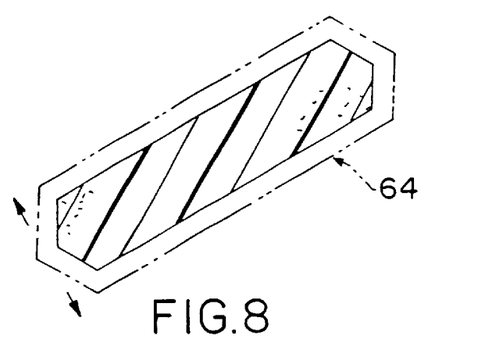
FIG. 8 shows, in cross-section, an ICR comprising a swellable, low modulus polymer.

FIG. 8 shows an ICR made of a low modulus, hydratable polymer such as those discussed above. Since these polymers often lose substantial mechanical strength upon hydration, these ICRs would be inserted into the intrastromal space prior to being hydrated or with the assistance of a tool either before or after hydration.

Figure 9A:
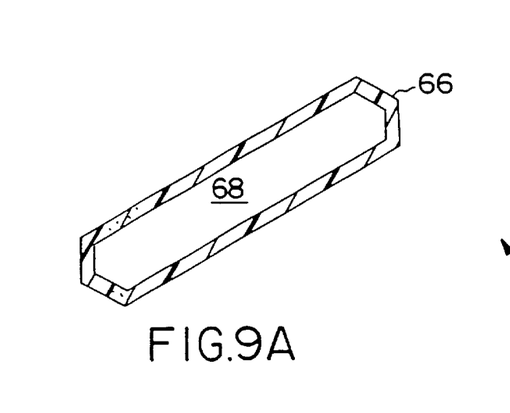
FIGS. 9A and 9B show, in cross-section, an ICR comprising a fillable shell which is nonhydrated in FIG. 9A and hydrated and swollen in FIG. 9B. The FIG. 9B ICR contains a fluid.

FIG. 9A shows an ICR made of a low modulus polymer system hydratable outer coating (66) and an inner cavity (68). This ICR may be inserted into the intrastromal space created by the dissector (as described above) as a covering on a tool similar to the dissector which created the intracorneal channel. Once in position the insertion tool is rotated out of the ICR leaving the shell within the stroma.

Alternatively, the ICR may be introduced into the intrastromal channel as the dissector is fully rotated in place, attached to the leading edge of dissector, and pulled into the intrastromal channel as the dissector is rotated out of the eye.

Figure 9B:
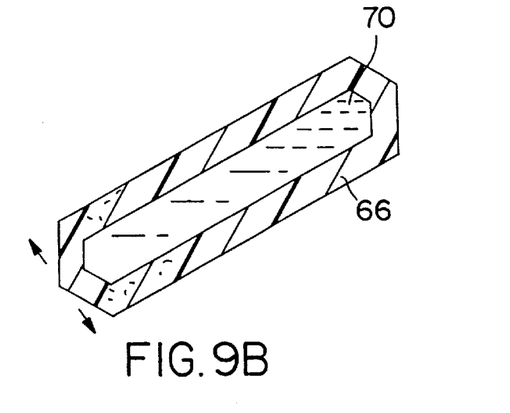

FIG. 9B shows the ICR of FIG. 9A upon completion of the hydration in that the outer covering (66) is swollen to its largest extent. Furthermore, the inner cavity (68) (FIG. 9A) may be filled with a biologic, drug or other liquid, or biologically active eye treatment material (70). These devices may be tied or otherwise connected at their point of insertion by known techniques.

The shell may be injected with a settable soft polymer core and allowed to expand to a desired thickness. Suitable injectable polymers are well known but include polyHEMA hydrogel, cross-linked collagen, cross-linked hyaluronic acid, siloxane gels, and organic-siloxane gels such as cross-linked methyl vinyl siloxane gels. The injected polymer sets after injection.

Figure 10A:
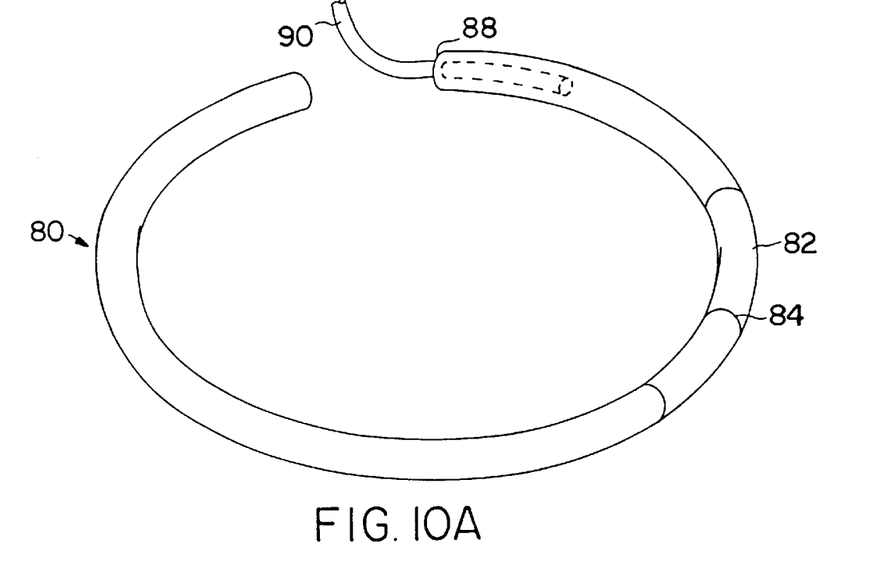
FIGS. 10A and 10B show a baffled soft ICR.
Figure 10B:
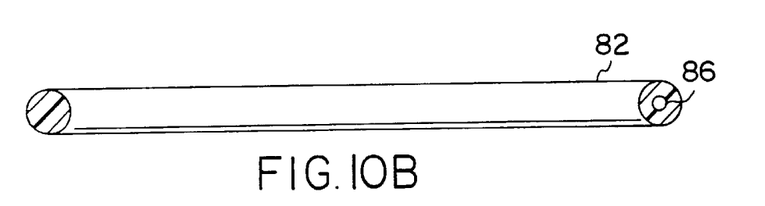

FIGS. 10A and 10B show a variation of the inventive ICR (80) in which a polymeric ring containing a number of chambers (82) separated by baffle walls (84) which may have an optional hole (86) in the baffle wall (84). Once the ICR is introduced into the eye, it may be filled with a drug or biologic material via injection with a suitable syringe through the ICR wall or into the end (88) of the tube. A settable polymer of the type discussed above may be introduced into the chambers in similar fashion if a ring of variable bulk is required. It is also appropriate to include a smaller fill tube (90) which extends through the end (88) of the tube (80) through the holes (86) in the baffle walls (84). In this way drugs, biologic agents, or settable polymers may be delivered in a specific fashion throughout the ring as the fill tube is withdrawn from the ICR.

Figure 11:
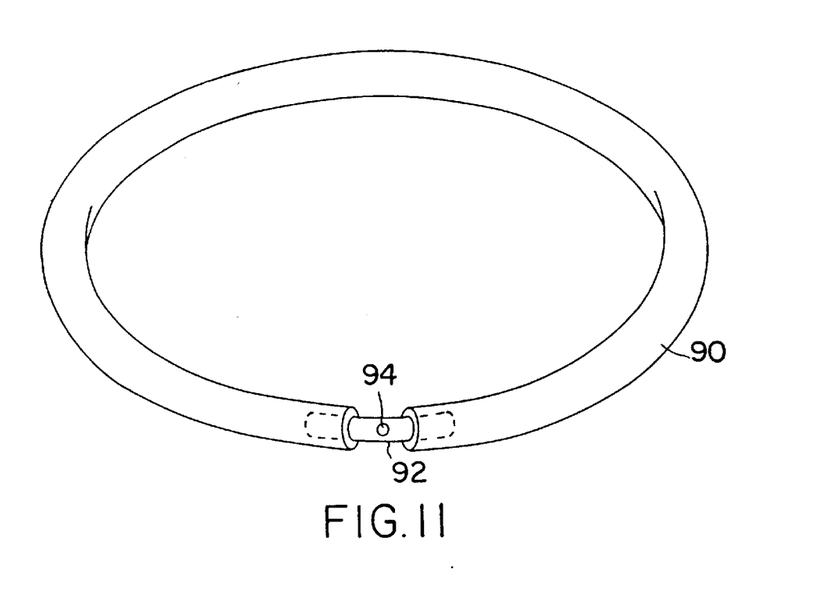
FIG. 11 shows an end-to-end ICR connector which permits introduction of drugs or a settable polymer.

FIG. 11 shows a connector (92) situated between the ends of an ICR (96). The ICR is a low-modulus polymer having a hollow center. The connector has a receiver port (94) suitable for introducing drugs, biologics, or settable polymers into the interior of the ICR. The connector has a passageway connecting the receiver port (94) into the ICR interior.

In the variation of the invention specified just above and shown in FIGS. 10A, 10B, and 11, the wall or outer covering of the ICR may be a hydratable low modulus polymer or an elastomer. If an elastomeric polymer is selected, the ICR may be injected with a settable polymer as specified.

The low modulus polymers used in this invention are often absorbent, particularly if they are hydratable, and may be infused with a drug or biologic agent which may be slowly released from the device after implantation of the ICR. For instance, the low modulus polymer may be loaded with a drug such as dexamethasone to reduce acute inflammatory response to implanting the device. This drug helps to prevent undesirable scarring or vascular in growth toward the ICR. Similarly, heparin, corticosteroids, antimitotics, antiinflammatories, antithrombgenics, and antiangiogenesis factors (such as nicotine adenine dinucleotide (NAD$^+$)) may be included to reduce or prevent angiogenesis and inflammation.

Clearly, there are a variety of other drugs suitable for inclusion in the ICR. The choice will depend upon the use to which the drugs are put.

The terms and expressions which have been used in the description above are used only as terms of description and not of limitation. There is no intention of excluding equivalents of the features shown or described. It is recognized that one having ordinary skill in this art would perceive equivalence to the inventions claimed below, which equivalence would within the spirit of the invention as expressed above.

I claim as my invention:

1. An intracorneal implant adapted for implantation within a surgically formed channel in the stroma of a human cornea and configured to alter the shape of the cornea to effect refractive correction of an eye, said implant comprising a ring which comprises an inner polymeric portion and at least one outer portion which comprises a hydratable, low elastic modulus physiologically compatible polyer the inner portion and the outer portion comprising different materials.

2. The implant of claim 1 where the polymer of the outer portion is sufficiently cross-linked or reinforced such that it does not swell when hydrated.

3. The implant of claim 2 where said ring further comprises a drug or biologic agent.

4. The implant of claim 2 where the ring further comprises a drug and said drug is an antiinflammatory or antithrombogenic agent.

5. The implant of claim 2 where the ring further comprises a drug and said drug is selected from dexamethosone, heparin, corticosteroids, antimitotics, antiinflammatory and antiangiogenesis factors.

6. The implant of claim 1 where the polymer of the outer portion will swell when hydrated.

7. The implant of claim 6, where said ring is adapted for delivery into an intrastromal channel in a dehydrated state such that subsequent hydration within said channel causes said ring to swell.

8. The implant of claim 6 wherein said outer portion covers only selected portions of said inner portion.

9. The implant of claim 1 additionally comprising an ocular lubricant.

10. The implant of claim 9 where the ocular lubricant is selected from hyaluronic acid, methylethylcellulose, dextran solutions, glycerine solutions, polysaccharides, or oligosaccharides.

11. The implant of claim 1, wherein said polymer of the outer portion comprises at least one polymer selected from polyhydroxyethyl methacrylate, polyvinylpyrrolidone, polyurethane, and polymerized vinyl pyrrolidone and methylmethacrylate.

12. The implant of claim 1, wherein the polymer of the outer portion comprises an elastomer.

13. The implant of claim 12, wherein the elastomer comprises an elastomeric polymer having a modulus of elasticity below 3.5 kpsi and selected from the group consisting of latex rubber, a colloid of polyester and polyether, polyurethane, low molecular weight silicone, and isoprene.

14. The implant of claim 1, wherein the polymer of the outer portion comprises a hydrogel having a modulus of elasticity below 3.5 kpsi.

15. The implant of claim 1 wherein the ring is a split ring.

16. The implant of claim 15, wherein said polymer of the outer portion is a biological polymer.

17. The implant of claim 16, wherein the biological polymer comprises a polymer selected from the group consisting of cross-linked dextran, hyaluronic acid, and heparin.

18. The implant of claim 15 wherein the outer portion covers at least substantially all of the inner portion.

19. The implant of claim 1 wherein the inner portion comprises a single layer.

20. The implant of claim 1 wherein the outer portion has a region whose thickness differs from the thickness of a second region of the outer portion.

21. The implant of claim 1 wherein the inner polymeric portion comprises a high elastic modulus physiologically compatible polymer.

22. The implant of claim 21 wherein the high elastic modulus physiologically compatible polymer comprises a polymer selected from the group consisting of PMMA, PTFE, silicone, polycarbonate, a polyolefin selected from polyethylene, polypropylene, polybutylene, and mixtures or interpolymers thereof.

23. An intrastromal implant adapted for implantation within a human cornea and configured to alter the shape of the cornea to effect refractive correction of an eye, said implant comprising an arcuate member having ends and which comprises an inner polymeric portion and at least one outer portion which comprises a hydratable, low elastic modulus physiologically compatible polymer.

24. The implant of claim 23 where the polymer of the outer portion is sufficiently cross-linked or reinforced such that the polymer does not swell when hydrated.

25. The implant of claim 24 where said implant further comprises a drug or biologic agent.

26. The implant of claim 24 where the implant further comprises a drug and said drug is an antiinflammatory or antithrombogenic agent.

27. The implant of claim 24 where the implant further comprises a drug and said drug is selected from dexamethosone, heparin, corticosteroids, antimitotics, antiinflammatory and antiangiogenesis factors.

28. The implant of claim 23 where the polymer of the outer portion will swell when hydrated.

29. The implant of claim 28, where said implant is adapted for delivery into an intrastromal channel in a dehydrated state such that subsequent hydration within said channel causes said ring to swell.

30. The implant of claim 28 wherein said outer portion covers only selected portions of said inner portion.

31. The implant of claim 23 additionally comprising an ocular lubricant.

32. The implant of claim 31 where the ocular lubricant is selected from hyaluronic acid, methylethylcellulose, dextran solutions, glycerine solutions, polysaccharides, or oligosaccharides.

33. The implant of claim 23, wherein said polymer of the outer portion is a biological polymer.

34. The implant of claim 33, wherein the biological polymer comprises a polymer selected from the group consisting of cross-linked dextran, hyaluronic acid, and heparin.

35. The implant of claim 23, wherein said polymer of the outer portion comprises at least one polymer selected from polyhydroxyethyl methacrylate, polyvinylpyrrolidone, polyurethane, and polymerized vinyl pyrrolidone and methylmethacrylate.

36. The implant of claim 23, wherein the polymer of the outer portion comprises an elastomer.

37. The implant of claim 36, wherein the elastomer comprises an elastomeric polymer having a modulus of elasticity below 3.5 kpsi and selected from the group consisting of latex rubber, a colloid of polyester and polyether, polyurethane, low molecular weight silicone, and isoprene.

38. The implant of claim 23, wherein the polymer of the outer portion comprises a hydrogel having a modulus of elasticity below 3.5 kpsi.

39. The implant of claim 23 wherein the outer portion covers at least substantially all of the inner portion.

40. The implant of claim 39 wherein the outer portion of the implant comprises a single layer.

41. The implant of claim 23 wherein the outer portion comprises a single layer.

42. The implant of claim 41 wherein the inner portion comprises a second layer.

43. The implant of claim 23 wherein the outer portion has a region whose thickness differs from the thickness of a second region of the outer portion.

44. The implant of claim 23 wherein the inner polymeric portion comprises a high elastic modulus physiologically compatible polymer.

45. The implant of claim 44 wherein the high elastic modulus physiologically compatible polymer comprises a polymer selected from the group consisting of PMMA, PTFE, silicone, polycarbonate, a polyolefin selected from polyethylene, polypropylene, polybutylene, and mixtures or interpolymers thereof.

* * * * *

UNITED STATES PATENT AND TRADEMARK OFFICE

CERTIFICATE OF CORRECTION

PATENT NO. : 5,888,243

DATED : March 30, 1999

INVENTOR(S) : Thomas A. Silvestrini

It is certified that error appears in the above-identified patent and that said Letters Patent is hereby corrected as shown below:

Correct the Inventor's name from "Silverstrini" to --Silvestrini--.

Signed and Sealed this

Tenth Day of October, 2000

Attest:

Q. TODD DICKINSON

*Attesting Officer*   *Director of Patents and Trademarks*